United States Patent
Luftensteiner et al.

(10) Patent No.: US 9,011,911 B2
(45) Date of Patent: *Apr. 21, 2015

(54) HIGH DRUG LOAD TABLET

(71) Applicants: Christian-Peter Luftensteiner, Weil am Rein (DE); Jean-Claude Bianchi, Blotzheim (FR); Joerg Ogorka, Steinen (DE); Oskar Kalb, Loerrach (DE)

(72) Inventors: Christian-Peter Luftensteiner, Weil am Rein (DE); Jean-Claude Bianchi, Blotzheim (FR); Joerg Ogorka, Steinen (DE); Oskar Kalb, Loerrach (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/162,237

(22) Filed: Jan. 23, 2014

(65) Prior Publication Data

US 2014/0135340 A1 May 15, 2014

Related U.S. Application Data

(63) Continuation of application No. 13/423,990, filed on Mar. 19, 2012, which is a continuation of application No. 12/764,696, filed on Apr. 21, 2010, now abandoned, which is a continuation of application No. 10/512,171, filed as application No. PCT/EP03/04151 on Apr. 22, 2003, now abandoned.

(30) Foreign Application Priority Data

Apr. 23, 2002 (GB) .................................. 0209265.8

(51) Int. Cl.
| | |
|---|---|
| A61K 9/20 | (2006.01) |
| A61K 9/28 | (2006.01) |
| A61K 31/497 | (2006.01) |
| A61K 31/505 | (2006.01) |
| A61K 31/185 | (2006.01) |
| A61K 31/506 | (2006.01) |
| B29C 43/00 | (2006.01) |

(52) U.S. Cl.
CPC .............. *A61K 9/28* (2013.01); *A61K 9/2013* (2013.01); *A61K 9/2054* (2013.01); *A61K 31/505* (2013.01); *A61K 31/185* (2013.01); *A61K 31/506* (2013.01); *B29C 43/003* (2013.01)

(58) Field of Classification Search
None
See application file for complete search history.

(56) References Cited

U.S. PATENT DOCUMENTS

| | | | |
|---|---|---|---|
| 3,453,368 A | 7/1969 | Magid | |
| 4,562,024 A | 12/1985 | Rogerson | |
| 4,666,705 A | 5/1987 | DeCrosta et al. | |
| 5,069,910 A | 12/1991 | Kovacic et al. | |
| 5,453,283 A | 9/1995 | Munch et al. | |
| 5,506,248 A | 4/1996 | Nikfar et al. | |
| 5,605,889 A | 2/1997 | Curatolo et al. | |
| 5,635,208 A | 6/1997 | Parekh | |
| 5,798,120 A | 8/1998 | Tomohisa et al. | |
| 5,861,141 A | 1/1999 | Mendizabal | |
| 5,879,706 A | 3/1999 | Carter et al. | |
| 5,916,593 A | 6/1999 | De Haan et al. | |
| 6,106,865 A | 8/2000 | Staniforth et al. | |
| 6,123,964 A | 9/2000 | Asgharnejad et al. | |
| 6,294,197 B1 | 9/2001 | Wagner et al. | |
| 6,294,198 B1 * | 9/2001 | Vilkov | 424/465 |
| 6,342,247 B1 | 1/2002 | Ku et al. | |
| 6,498,153 B1 | 12/2002 | Cady et al. | |
| 7,041,313 B1 * | 5/2006 | Dietrich et al. | 424/451 |
| 7,695,735 B2 | 4/2010 | Chauveau et al. | |
| 7,850,993 B2 | 12/2010 | Tojo et al. | |
| 2001/0014352 A1 | 8/2001 | Batra et al. | |
| 2001/0038852 A1 | 11/2001 | Kolter et al. | |
| 2003/0045580 A1 | 3/2003 | Einig | |

FOREIGN PATENT DOCUMENTS

| | | |
|---|---|---|
| CA | 2 093 203 A | 11/2002 |
| EP | 0189114 B1 | 8/1991 |
| EP | 0 253 104 B1 | 10/1991 |
| EP | 0 564 409 | 3/1993 |
| EP | 0890359 A | 1/1999 |
| EP | 0747050 B1 | 9/2003 |
| JP | A-63-267731 | 11/1968 |
| JP | A-6-501685 | 9/1995 |
| JP | A-10-259201 | 9/1996 |

(Continued)

OTHER PUBLICATIONS

Kantarjian et al. (Seminars in Oncology 2001 28 S17:9-18.*

(Continued)

*Primary Examiner* — Juliet Switzer
*Assistant Examiner* — Caralynne Helm
(74) *Attorney, Agent, or Firm* — Matthew Mulkeen

(57) ABSTRACT

The present invention pertains to a high drug load tablet comprising an active ingredient Compound I of formula

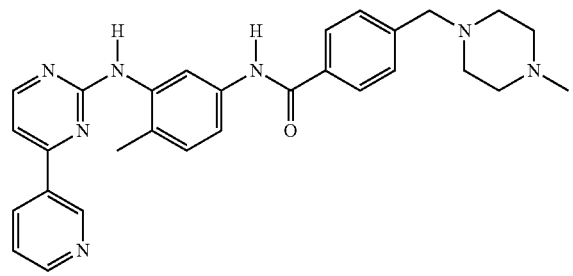

or a pharmaceutically acceptable salt thereof in an amount from about 30% to 80% in weight of the active moiety based on the total weight of the tablet.

11 Claims, No Drawings

(56) References Cited

FOREIGN PATENT DOCUMENTS

| | | |
|---|---|---|
| JP | A-2001-278813 | 3/2001 |
| JP | 2001-139462 | 5/2001 |
| JP | 2002-12540 | 1/2002 |
| KR | 2001-0090831 | 10/2001 |
| WO | WO8900424 | 1/1989 |
| WO | WO 90/08542 | 8/1990 |
| WO | WO94/27557 | 12/1994 |
| WO | 95/09852 | 4/1995 |
| WO | WO 95/09852 | 4/1995 |
| WO | WO95/09852 | 4/1995 |
| WO | WO 96/22082 | 7/1996 |
| WO | WO 97/49394 | 12/1997 |
| WO | WO 97/49394 A2 | 12/1997 |
| WO | WO 9749394 A2 | 12/1997 |
| WO | 99 03854 | 1/1999 |
| WO | WO 99/03854 | 1/1999 |
| WO | WO99/03854 A1 | 1/1999 |
| WO | WO 99/15155 | 4/1999 |
| WO | WO 99/25321 | 5/1999 |
| WO | WO 99/44580 | 9/1999 |
| WO | WO 00/27398 | 5/2000 |
| WO | WO 00/59500 | 10/2000 |
| WO | WO 01/08686 | 1/2001 |
| WO | WO 01/19383 | 3/2001 |
| WO | WO01/41733 | 6/2001 |
| WO | 01 47507 | 7/2001 |
| WO | WO01/47507 | 7/2001 |
| WO | WO 01/47507 | 7/2001 |
| WO | WO 01/70225 | 9/2001 |
| WO | WO0164183 | 9/2001 |
| WO | WO01/97805 | 12/2001 |
| WO | WO02/067993 | 9/2002 |

OTHER PUBLICATIONS

Becker D. et al., "Effectiveness of Binders in Wet Granulation: A Comparison Using Model Formulations of Different Tabletability," Drug Development and Industrial Pharmacy, vol. 23(8), pp. 791-808 (1997).
Chowhan Z.T. et al., "Effect of Intergranular versus Intragranular Cornstarch on Tablet Friability and In Vitro Dissolution," Journal of Pharmaceutical Sciences, vol. 72(9), pp. 983-988 (1983).
Deak, D. et al., "Use of different cellulose derivatives for the preparation of tablets with a high active agent content," S.T.P. Pharma Sciences, vol. 9(6), pp. 525-529 (1999).
Hagers Handbuch, $5^{th}$ revised edition, pp. 724-737 ((1991).
Wade, A. et al. (eds.) Handbook of Pharmaceutical Excipients, $2^{nd}$ edition, American Pharmaceutical Association, Washington; The Pharmaceutical Press, London, pp. 84-87, 229-232, 143-144, 424-427, 280-282 (1994).
MIMS (2002).
Muti H. et al., "Effects of Binders and Moisture Content on the Disintegration, Hardness and Friability of Paracetamol and Orphenadrine Citrate Tablets," Drug Devleopment and Industrial Pharmacy, vol. 15(2), pp. 2017-2035 (1989).
Lund, Waiter (ed.), The Pharmaceutical Codex, $12^{th}$ Edition, Principles and Practice of Pharmaceutics, Pharmaceutical Press, London, pp. 2-211, 198-203 (1994).
Aulton M. (ed.) Pharmaceutics: The Science of Dosage Form Design, first edition, Churchill Livinstone, Chapts. 18 and 39 (1988).
Parikh D.M. (ed.) Handbook of Pharmaceutical Granulation Technology, Marcel Dekker, New York USA, Chapter 2, pp. 2-23 (1997).
Gennaro A.R. (ed.) Remington: The Science and Practice of Pharmacy, $20^{th}$ Edition, Lippincott Williams & Wikkings, Chapter 45 (2000).
Ritschel W.A. et al., Die Tablette, 2nd edition, pp. 63-67 (2002).
Ritschel W.A. et al., Die Tablette, pp. 77-170.
Lachman L. et al., (eds.) The Theory and Practice of Industrial Pharmacy, $2^{nd}$ ed., Chapt. 11—Tablets, pp. 321-358 (1976).
The United States Pharmacopeia 24, pp. 2117-2121 (2000).
Lieberman et al., (eds.) Pharmaceutical Dosage Forms: Tablets, vol. 2, Marcel Dekker, Inc., NY, pp. 1-20 (1990).
Lieberman et al. (eds.) Pharmaceutical Dosage Forms: vol. 1, $2^{nd}$ edition, Chapters 3 and 4, pp. 131-246 (1990).
Physicians' Desk Reference, $56^{th}$ edition (2002).
Murav'jev I.A., "Technologija lekarstv," Medicina, vol. 1, pp. 342-345 (1980) (English translation attacged).
Ansel et al., Pharmaceutical Dosage Forms and Drug Delivery Systems, Sixth Edition, pp. 192-197 (A Lea & Febiger Book) (1995).
Pharmaceutical Dosage Forma: Tablets, vol. 1, Second Edition, H.A. Lieberman, pp. 79-81, 94, 113-116 and 121-122, 1989.
Remington's Pharmaceutical Sciences; 1995, 19, p. 1616 and 1623.
Mauro et al, The Oncologist 6:233-238, 2001.
Druker, 'Long-term benefits of Imatinib . . . ' Journal of Clinical Oncology, 2006 ASCO, vol. 24 No. 189 (Jun. 20 supplement) 2008: 6506.
Druker, 'Five-year follow up of patients receiving Imatinib for chronic myeloid leukemia' NEJM, 355;23, Dec. 7, 2006.
Capaugel, The Capsule Advantage, http:www.capsugel.com/about/advantage/php, 2009.
MIMS Apr. 2004, p. 1 and 338.
MIMS Oct. 2004, p. 1 and 353.
Novartis, Center for Drug Evaluation and Research, NDA 21-335, Final printed labeling. Sep. 5, 2001,
Glivec-en.doc, 100mg capsules.
Cohen, 'Gleevec for the treatment of chronic . . . ' The Oncologist, FDA Commentary. 2002;7:390-392.
Lee, 'Overview of Drug Product Development' Current Protocols in Pharmacology (2001) 7.3.1-7.3.10.
Carstensen, Advanced Pharmaceutical Solids, 2001, p. 375.
Hansell, Narrowing the gap between clinical capsule . . . Pharmaceutical Technology, May 2009 Issue.
Gibson, Pharmaceutical Preformulation and Formulation. 2001. pp. 441-446.
Aulton, Pharmaceutics. The Science of Dosage Form Design, $2^{nd}$ Edit. 2002. p. 449-450.
Mullen, Email to Richard Gilard. Oct. 9, 2010.
Gibbs, Research Service.
Lachman. The Theory and Practice of Industrial Pharmacy. $3^{rd}$ edit. 1986. p. 293-294.
Gamlen. Declaration in matter of EP 1 501 485. Dec. 9, 2010.
Rue, Peter. Declaration in matter of EP 1 501 485. May 10, 2010.
US Pharmacopeia. The National Formulary, Jan. 1, 2002.
Baneker, Declaration. Oct. 6, 2010.
Kibbe. Handbook of Pharmaceutical Excipients. $3^{rd}$ edition, 2000. p. 163-164.
Nikolova, 'Bioequlvalence, safety, and tolerability . . . ' Cancer Chemother, Pharmacol (2004) 53:433-438.
Glivec-en.doc. 100mg capsules. Sep. 16, 2010.
Ritschel et al., Die Tabletter, $2^{nd}$ edition, pp. 64-65, 2002, (D4) (English Translation).
Ritschel W.A., Die Tabletter, pp. 77-79, 1966, (D3) (English Translation).
"General Rules for Preparations", A Guide to the Japanese Pharmacopoeia, Thirteenth Edition, Hirokawa Shoten, (1996) A97-A-104 (compare with No. 98 which is $14^{th}$ edition).
A Collection of Medical Drug Package Inserts, Nagase Medicals Co., Ltd. (1998), pp. 39, 40, 81-84, 91, 92, 103, 104, 111-114, 123, 124, 179, 199-202, 251, 262, 263-265, 275 and 276 (In Japanese).
Fude CUI, China Medical Science Press, Aug. 2002, pp. 105-106.
Caramella, Carla et al., International Journal of Pharmaceutics, vol. 44, pp. 177-186, 1988.
Physicians' Desk Reference, ed. 61, 2007. p. 2227.
Note for Guidance on the Investigation of Bioavailabliity and Bioequivalence, point 2.5, Essentially similar products (The European Agency for the Evaluation of Medicinal Products).
Remington's Pharmaceutical Sciences, 1980, 16th Edition, pp. 1560-1563.
Porter, "Coating of pharmaceutical dosage forms", in Remington: the science and Practice of Pharmacy, Gennaro ed. Easton Mack Publishing Co., pp. 1650, 1995.

(56) References Cited

OTHER PUBLICATIONS

Bandelin, "Compressed tablets by wet granulation", in Pharmaceutical Dosage Forms: Tablets Lieberman et al., eds. New York:Marcel Dekkar, Inc., pp. 131-137, 1989.

Pharmaceutical Dosage Forms: Tablets, vol. 1, Second Edition, Edited by Herbert A. Lieberrman et al, p. 174.

Rudnic E.M. et al: "Studies of the utility of cross linked polyvinylpolypyrrolidine as a tablet disintegrant", Drug Development and Industrial Pharmacy, 6(3), 291-309 (1980).

Handbook of Pharmaceutical Excipients, Sixth edition Edited by Raymond C. Rowe et al, 2009 p. 208.

Kantajarian et al.,"Imatinib Mesylate: Clinical Results in Philadelphia Chromosome-Positive Leukemias", Seminars in Oncology, vol. 28, No. 5, Suppl. 17, pp. 9-18, (2001).

Vasenthavada M. et al., "Application of Melt Granulation Technology Using Twin-screw Extruder in Development of High-dose Modified-Release Tablet Formulation", Journal of Pharmaceutical Sciences, online publication, pp. 1-12, 2010.

Durig et al., "An Investigation into the Erosion Behaviour of a High Drug-load (85%) Particulate System Designed for an Extended-release Matrix Tablet. Analysis of Erosion Kinetics in Conjunction with Variations in Lubrication, Porosity and Compaction Rate", J. Pharm. Pharmacol. vol. 51, pp. 1085-1092, 1999.

Lieberman, Pharmacuetical Dosage Forms, Second edit. vol. 1., pp. 94, 1989.

Drug Label of Tylenol Tablet, 500 mg, Exhibit 10-1, Downloaded Jan. 25, 2013.

Information on API of Tylenol Tablet, "Tylenol Tablet 500 mg (Acetaminophen) Tylenol Tab. 500 mg", BitDrugInfo, http://www.druginfo.co.kr/detail/product.aspx?pid=9693, Downloaded Dec. 28, 2012.

Information on Product Approval for Tylenol Tablet, "Tylenol Tablet 500 mg (Acetaminophen) Tylenol Tab. 500 mg", Exhibit 10-3., http://www.druginfo.co.kr/detail/product.aspx?pid=9693 , Downloaded Dec. 28, 2012.

Miu, Lide, "Pharmaceutics", China Medical Science Press 2nd edition, pp. 263-264, Jun. 1999, Translated in English [PN092043].

Luo, Mingsheng and Gao, Tianhui (editor), "Pharmaceutical Excipients" Sichuan Science and Technology Press, $1^{st}$ Edition, pp. 78, Mar. 1993, Translated in English.

"Kagaku-Ryoho no Ryoiki" (Antibiotics & Chemotherapy) vol. 18, No. 4, p. 85 to p. 86 (published on Mar. 25, 2002), Iyaku (Medicine and Drug) Journal Co., Ltd.

Practice vol. 11, No. 1 p. 60 to 66 (published in 1994).

"Designing and Assessment of oral administrating agents (our translation)" JIHOU Co. (Published on Feb. 10, 1995), "Chapter 2, 2.2) Selection of candidate compounds for a pharmaceutical agent".

Novartis Pharma KK. Press Release (Japanese).

The Pharmaceutical Reference Nagase Medicals Co., Ltd (Japanese).

Experts of the Japanese Pharmacopoeia, "The 14th revision Japanese Pharmacopoeia Guide", Hirokawa-shoten, General Rules of formulations 14 Tablets (Japanese).

Journal of Pharmaceutical Science and Technology, vol. 60, p. 230.

Journal of the Takeda Research Laboratories, vol. 43, pp. 111-115.

\* cited by examiner

HIGH DRUG LOAD TABLET

The present invention relates to pharmaceutical tables comprising 4-(4-methylpiperazin-1-ylmethyl)-N-[4-methyl-3-(4-pyridin-3-yl)pyrimidin-2-ylamino)phenyl]-benzamide or pharmaceutically acceptable salts thereof and is hereinafter referred as Compound I.

Compound I has the formula (1)

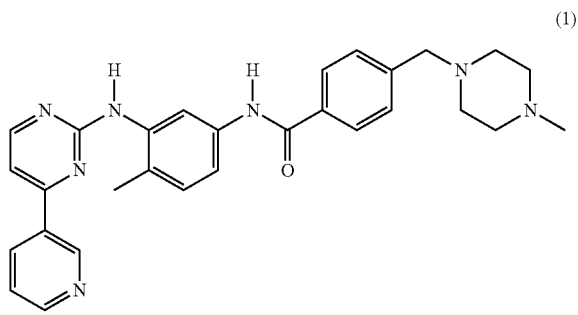 [SMILES: Cc1ccc(NC(=O)c2ccc(CN3CCN(C)CC3)cc2)cc1Nc1nccc(-c2cccnc2)n1]

Compound I free base and its acceptable salts thereof are disclosed in the European Patent application 0564409. Compound I mesylate and Compound I mesylate alpha and beta crystal forms are disclosed in International Patent application WO 99/03854.

Typically, prescribed daily dosages of Compound I mesylate for the treatment of leukemia are high, e.g. 400-800 mg in adults. Thus, there is a need for an oral dosage form which is convenient to administer and provides a daily dosage amount of Compound I.

Accordingly, the present invention provides a tablet with high drug loading comprising a pharmacologically effective amount of Compound I or a pharmaceutically acceptable salt thereof present in an amount of from about 30% to 80%, e.g. at least about 35, 40, 45, 50 or 55% to about e.g. 60, 65, 70, 75 or 80%, preferably more than 55%. In particular, the amount of Compound I may vary from 45 to 80%, e.g. 50 to 70% in weight based on the total weight of the tablet.

Compound I may be in the free base form or pharmaceutically acceptable salts thereof, e.g. monomesylate form. The active moiety corresponds to Compound I in the free base form. For example, 119.5 mg of Compound I mesylate salt correspond to 100 mg of Compound I free base active moiety.

The present invention also provides a tablet comprising
(a) a pharmacologically effective amount of compound I, and
(b) at least one pharmaceutically acceptable excipient suitable for the preparation of tablets wherein the amount of Compound I or pharmaceutically acceptable salt thereof calculated as the percentage of the content in weight of the active moiety based on the total salt thereof, is from about 30% to 80%, e.g. at least about 35, 40, 45, 50 or 55% to about e.g. 60, 65, 70, 75 or 80%, preferably more than 55%. In particular the amount of Compound I may vary from 45 to 80%, e.g. 50 to 70% in weight of the active moiety based on the total weight of the tablet.

In another aspect, the present invention provides a tablet wherein the Compound I is in crystalline form.

In a further aspect of the invention, the monomesylate salt of Competed I is used.

In a preferred embodiment of the invention, the monomesylate salt of Compound I is in crystalline form, e.g. alpha or beta crystal form, most preferably, the monomesylate salt of Compound I is in the beta crystal form.

One or more pharmaceutically acceptable excipients may be present in the tablets, e.g. those conventionally used, e.g. (1.1) at least one binder, e.g. microcrystalline cellulose, hydroxypropylmethyl cellulose, (1.2) at least one disintegrant, e.g. cross-linked polyvinylpyrrolidinone, e.g. Crospovidone®, (1.3) at least one glidant, e.g. colloidal silicon dioxide, (1.4) at least one lubricant, e.g. magnesium stearate and/or (1.5) basic coating. In the tablet according to the present invention, microcrystalline cellulose is used as a binder.

Reference is made to the extensive literature on the subject for these and other excipients and procedures mentioned herein, see in particular Handbook of Pharmaceutical Excipients, Third Edition, edited by Arthur H. Kibbe, American Pharmaceutical Association, Washington, USA and Pharmaceutical Press, London; and Lexikon der Hilfsstoffe für Pharmazie, Kosmetik and angrenzende Gebiete edited by H. P. Fiedler, 4th Edition, Edito Cantor, Aulendorf and earlier editions which are incorporated herein by reference.

Binders (1.1) include but are not restricted to starches, e.g. potato, wheat or corn starch; microcrystalline cellulose, e.g. products such as Avicel®, Filtrak®, Heweten® or Pharmacel®; hydroxypropyl cellulose; hydroxyethyl cellulose; hydroxypropylmethyl cellulose, e.g. hydroxypropylmethyl cellulose-type 2910 USP, hypromellose, and polyvinylpyrrolidone, e.g. Povidone® K30 from BASF. Preferably, hydroxypropylmethyl cellulose-Type 2910 USP is used.

Suitable disintegrants (1.2) according to the invention include but are not restricted to maize starch; CMC-Ca; CMC-Na; microcrystalline cellulose; cross-linked PVP, e.g. as known and commercially available under the trade names Crospovidone®, Polyplasdone®, available commercially from the ISP company, or Kollidon® XL; alginic acid; sodium alginate; and guar gum. Preferably, cross-linked PVP, e.g. Crospovidone® is used.

As glidants (1.3), one or more of the following may be used: silica; colloidal silica, e.g. colloidal silica anhydrous, e.g. Aerosil® 200, magnesium trisilicat, powdered cellulose, starch and talc. Preferably colloidal silica anhydrous or/and colloidal silicon dioxide are used.

As lubricants (1.4) one or more of the following may be used Mg-, Al- or Ca-stearate, PEG 4000-8000 and/or talc. Preferably magnesium stearate is used.

One or more of these excipients can be selected and used having regard to the particular desired properties of the tablet by routine experimentation.

According to the present invention, the amount of binder (1.1) may vary within a range of from about 1 to 40%, preferably 1 to 30%, in particular 1 to 25% in weight based on the total weight of the tablet.

The amount of disintegrant (1.2) may vary within a range of from to 5 to 40%, e.g. 10 to 35% in weight based on the total weight of the tablet.

The amount of glidant (1.3) may vary within ranges of from 0.1 to 10%, in particular 0.1 to 5%, e.g. 0.5 to 3% in weight based on the total weight of the tablet or 2 to 4% in weight based on the total weight of the tablet.

The amount of lubricant (1.4) may vary within a range of from 0.1 to 5%, e.g. 0.5 to 2% in weight based on the total weight of the tablet.

the amount of basic coating (1.5) may vary from 1 to 10%, preferably from 1.5 to 5% in weight based on the total weight of the tablet.

It will be appreciated that any given excipient may serve more than one function e.g. as disintegrant, binder, glidant, and/or lubricant.

In a preferred aspect of the invention, the tablet comprises the following excipients, one or more binders in a total amount of about 1% to 25% in weight based on the total weight of the tablet, one or more disintegrants in a total amount of about 10% to 35% in weight based on the total weight of the tablet, one or more glidants in a total amount of about 0.5% to 3% in weight based on the total weight of the tablet, and/or one or more lubricants in a total amount of about 0.5% to 2% in weight based on the total weight of the tablet.

The absolute amounts of each excipient and the amounts relative to other excipients is similarly dependent on the desired properties of the tablet and may also be chosen by routine experimentation. For example, the tablet may be chosen to exhibit accelerated and/or delayed release of Compound I with or without quantitative control of the release of active agent. Preferably the tablet is chosen to exhibit immediate release of the compound I, e.g. the Compound I monomesylate salt beta crystal form.

The present inventors have encountered difficulties in the production of Compound I tablets due to high friability values and poor abrasion resistance. Further, the flexibility in the quantity of excipients, e.g. disintegrants, is limited due to the high drug load of the product. Thus, there still exists a need for commercially acceptable Compound I dosage forms for oral administration with good patient convenience and acceptance.

In accordance with the present invention, it has now unexpectedly been found that stable and convenient galenic tablets comprising Compound I are obtainable. The present Applicants have found that pharmaceutically acceptable oral solid dosage forms in the form of tablets, being particularly convenient to administer and stable, may be obtained by preparation of tablets by compression methods. More specifically, the tablets of the invention may be prepared by granulation, preferably wet-granulation, followed by compression methods. Compound I, especially the mesylate salt, exhibits high particle size, e.g. 60% of the Compound I starting material having a particle size greater or equal to 100 µm, e.g. 90% of the particles are smaller or equal to 420 µm. Wet-granulation process is usually performed with a starting material of particle size lower than 100 µm.

It is a characteristic of the tablet according to the invention that it contains a high content of Compound I given the relatively small amount of excipients. This enables the production of physically small tablets. The total amount of excipients in a given unit dosage may be about 70% or less by weight based on the total weight of the tablets more particularly about 50% or less. Preferably the excipient content is in the range of about 30 to 55%, more particularly 35 to 50% in weight based on the total weight of the tablet.

Tablets according to the invention surprisingly provide for the administration of Compound I in a smaller size than was hitherto possible for a gives unit dose of Compound I. The tablets of the invention are, despite the high drug loading, small, and, therefore, convenient to administer. This leads to a better patient compliance.

In another embodiment this invention provides a tablet comprising from 50 mg to 600 mg Compound I, e.g. of from 100 mg to about 400 mg. Most preferably, tablets according to the invention are tablets containing 100 mg and/or tablets containing 400 mg of Compound I.

Accordingly, the present invention provides for tablets containing an amount of Compound I mesylate, e.g. Compound I mesylate alpha crystal form and/or Compound I mesylate beta crystal form, equal to 100 mg; and/or 400 mg of Compound I free base. Most preferably, the Compound I mesylate form used for the tablet according to the invention is the beta crystal form.

According to the invention, the process for the preparation of the tablets consists in forming an inner phase, mixing it together with an outer phase, compressing the obtained mixture and optionally coating the tablet.

The inner phase comprises Compound I. Preferably, the inner phase comprises Compound I and one or more excipients, more preferably one or more binders and most preferably the amount of one or more binders in the inner phase is ranging from about 1 to 30%, preferably 1 to 20% and more preferably 1 to 15%. The binders of the inner phase according to the invention are preferably microcrystalline cellulose and hydroxypropylmethyl cellulose. The amount of microcrystalline cellulose in the inner phase may vary from about 10 to 29%, in particular 12 to 14% in weight based on the total weight of the tablet. The amount of hydroxypropylmethyl cellulose in the inner phase may vary from 1 to 5%, preferably 1 to 2% in weight based or the total weight of the tablet. The Compound I and the pharmaceutically acceptable excipients of the inner phase are mixed together with water and the mixture is processed for granulation, e.g. using a wet high-shear granulator to form the wet-granulates. The wet-granulates may be then, dried, e.g. using a fluid bed dryer.

The present invention pertains to a process for the preparation of tablets comprising outer phase. The outer phase consists in a mixture of the inner phase with one or more excipients. The inner phase and one or more excipients of the outer phase are mixed together using, e.g. a diffusion mixer. Preferably, one or more binders are added. Most preferably cellulose microcrystalline is added. Even more preferably, microcrystalline cellulose is added in the range of 1 to 10% in weight based on the total weight of the tablet. In a preferred embodiment of the invention, in the outer phase, the amount of microcrystalline cellulose is around 5% in weight based on the total weight of the tablet. The outer phase according to the invention may also contain one or more disintegrants, most preferably Crospovidone®. In a preferred embodiment, the amount of disintegrant in the outer phase is ranging from about 10 to 30%, preferably 12 to 25%, most preferably about 15%.

In a particular aspect of the invention, one or more glidants are incorporated into the outer phase.

According to the invention, one or more lubricants are incorporated into the outer phase.

In a further aspect of the invention, tablets are performed by compression of the mixture of the inner and the outer phases using, e.g. a tablet press.

Optionally, the tablets may be coated, preferably as described herein after.

In one embodiment of the invention, the process for the preparation of a tablet which comprises
 (a) forming an inner phase comprising
  (i) mixing the Compound I together with pharmaceutically acceptable excipients
  (ii) wet-granulating
 (b) forming an outer phase comprising
  (iii) adding further pharmaceutically acceptable excipients to the inner phase and mixing;
 (c) forming the tablet by
  (iv) compressing the mixture obtained in step (iii) and, optionally
 (d) coating.

More specifically, in one aspect the present invention provides a process comprising:

(i) mixing the Compound I and pharmaceutically acceptable excipients, e.g. one or more binders, e.g. microcrystalline cellulose, in a high shear mixer;
(ii) adding water, subjecting the mixture to wetting/kneading, e.g. in a high shear mixer, screening using a screening mill with a rotating impeller, and drying, e.g. in a fluidized bed dryer;
(iii) adding pharmaceutically acceptable excipients, e.g. sieved excipients, such as one or more disintegrants, e.g. Crospovidone®, one or more binders, e.g. microcrystalline cellulose, one or more glidant, e.g. colloidal silicon dioxide, and mixing, e.g. in a diffusion mixer;
(iv) adding pharmaceutically acceptable excipients such as one or more lubricant e.g. magnesium stearate, sieving, e.g. hand-sieving, e.g. at 900 µm, and mixing, e.g. in a diffusion mixer;
(v) tabletting the mixture obtained in step (iv) by compression, e.g. in a conventional tablet press, e.g. in an EK-0 Korsch eccentric tabletting machine or a rotary tabletting machine, preferably a rotary machine and
(vi) coating, e.g. in a pan coater, e.g. Glatt, Accela.

By "core" is meant the granulate phase (steps (i) and (ii)) including the active drug Compound I and the outer phase consisting of the excipients.

By "total weight of the tablet" is meant the weight of a tablet being the inner and the outer phases and the coating (if any).

According to the invention, the coating process may be performed at low temperature, e.g. between 30 and 40° C., preferably between 32 and 39° C., most preferably at a temperature ranging from around 35 to around 38° C. The coating process may be performed with a spray rate preferably in the range of 30 to 105 g of coating dispersion per kg of cores per hour, preferably of 35 to 105 g. It has surprisingly been found that swelling of the disintegrants, e.g. Crospovidone®, nor sticking of the cores occurred during spraying of the coating mixture, as it would be expected by the person skilled in the art by processing at low temperatures.

Moreover, the tablets exhibit improved abrasion resistance. The physical and chemical stability may be tested in conventional manner, e.g. the tablets may be tested as such by measurement of dissolution, friability, disintegration time, assay for Compound I degradation products, appearance and/or microscopy, e.g. after storage at room temperature, i.e. 25° C., and/or storage at 40° C.

The tablet cores may vary in shape and be, for example, round, oval, oblong, cylindrical or any other suitable shape. A characteristic of tablets according to the invention is their small size having regard to the amount of Compound I or Compound I salt contained therein.

In a preferred embodiment of the invention tablets obtained by the compression method described above are round or oval. The edges of the tablets may be beveled or rounded. Most preferably, the tablets are ovaloid and/or round. The tablets according to the invention may be scored. The ovaloid tablet may be small in dimension e.g. 10 to 20 mm in length, preferably 15 to 30 mm, most preferably 17 to 19 mm; 5 to 10 mm in width, preferably 6.5 to 8 mm. The thickness of the tablet is from 4 to 8 mm, preferably 6 to 8 mm. Compression forces of between 10 to 20 kN are used to prepare the compressed tablet, preferably, 12 to 18 kN. Preferably, the ovaloid tablet contains 400 mg of Compound I. The round tablet may be of the following dimensions, e.g. 5 to 15 mm in diameter, preferably 7 to 10 mm, most preferably about 9 mm. The thickness of the tablet maybe from 2 to 5 mm, preferably 2.5 to 4 mm. Compression forces of between 6 to 18 kN are used to prepare the compressed tablet, preferably, 8 to 14 kN.

Preferably, the round tablet contains 100 mg of Compound I. Preferably the 100 mg tablet is a scored tablet, most preferably the tablet has a break score on one side.

The tablets of the invention comprising about 100 mg of Compound I may furthermore have a hardness of from about 30 to 140 N, e.g. 40 to 140N, 30 to 100 N, 40 to 100 N, preferably 50 to 80 N. The tablets of the invention comprising about 400 mg of Compound I may have a hardness of 100 to 270 N, e.g. 100 to 250 N, 160 to 270 N, 160 to 250 N, preferably 195 to 235 N.

The disintegration time of the tablet may be of about 20 min or less. Preferably, for the 100 mg Compound I tablet, the disintegration time is ranging from about 2 to 10 min, preferably 4 to 10 min, e.g. 4 to 8 min. For the 400 mg Compound I tablet, the disintegration time is, preferably ranging from about 7 to 15 min, preferably 8 to 15 min, e.g. 8 to 14 min.

The friability of the tablets is measured according to the US Pharmacopeia. The friability of the tablets according to the invention monitored following the recommendation of the US Pharmacopeia is 0%.

The tablets of the invention may furthermore be colored and/or the tablets or coating marked so as to impart an individual appearance and to make them instantly recognizable. The use of dyes can serve to enhance the appearance as well as to identify the tablets. Dyes suitable for use in pharmacy typically include carotinoids, iron oxides or chlorophyll. The tablets of the invention may be marked using an imprint code.

Procedures which may be used may be conventional or known in the art or based on such procedures e.g. those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeuitischen Praxis, 4th Ed. (Springer Verlag, 1971) and Remington's Pharmaceutical Sciences, 13th Ed., (Mack Publ., Co., 1970) or later editions.

The tablets of the invention are useful for human indication of Compound I, e.g. anti-tumor treatment, as indicated by standard tests. The activity and characteristics of the tablets of the invention may be indicated in standard clinical trials and/or animal trials.

The tablets of the invention are particularly useful for, e.g. treatment of non-malignant and malignant proliferative disorders, e.g. leukemias, gliomas, sarcomas, prostate-, breast-, gastro-intestinal-, lung-, ovary tumors.

The tablets of the invention comprising a pharmacologically effective amount of Compound I or Compound I salt may be administered as the sole active drug or with another active drug may be envisaged, e.g. together with simultaneous or separate administration of other drugs.

Furthermore, the tablets of the invention obtained are stable both to the production process and during storage, e.g. for 2 years or even 3 years in conventional packaging, e.g. sealed aluminium blister packs. Less than about 5%, e.g. 2 or 3% or less of Compound I or Compound I salt may degrade during this time as determined in conventional tests.

The tablets of the invention, e.g. the 100 and 400 mg tablets, are bioequivalent with the marketed hard gelatine capsules (100 mg) of Compound I. The administration of 400 mg of Compound I in hard gelatine capsules (4×100 mg) in the form of a single film coated tablet is well tolerated.

Depending on age, individual condition, mode of administration, and the clinical picture in question, effective doses, for example daily dosing of tablets of the invention comprising, e.g. 100-1000 mg, e.g. 100 to 800 mg, preferably 100 to 600 mg, especially 400 mg of Compound I, are administered to patients of about 70 kg body weight.

The invention relates also to a method for administering to a human subject in need of such a treatment, Compound I or a pharmaceutically acceptable salt thereof in the form of a tablet, once daily for a period exceeding 3 months. The invention relates especially to such method wherein a daily dose of 100 to 1000 mg, preferably 100 to 800 mg, especially 200 to 600 mg, preferably 400 mg, of Compound I is administered to an adult. It will be understood that the specific dose level for any particular patient will depend upon a variety of factors including the age, the body weight, general health, drug combination with one or more active drags, type and severity of the disease.

Accordingly in a further aspect the present invention provides a method of treating a subject which comprises administering a tablet according to the invention comprising a pharmacologically effective amount of Compound I salt to a subject in need of such a treatment, optionally with the simultaneous, sequential or separate administration of another drug e.g. a cyclosporin, a rapamycin, an ascomycin, corticosteroids, cyclophosphamide, azathioprine, methtrexate, brequinar, leflunomide, mizoribine, mycophenolic acid and/or mycophenolate mofetil.

When the tablets of the invention are co-administered with a combined therapy the dosages of the Compound I mesylate may be reduced e.g. to one-half to one-third their dosages when used alone.

The medicament package comprises tablets according to the invention and printed instructions directing that one or more tablets of Compound I be administered orally.

Following non-limitative examples illustrate the invention.

Example 1

Tablet Formulation (100 mg Tablet)

| Composition per dosage form unit and quantity per batch | | | | | |
|---|---|---|---|---|---|
| Component | | Composition per unit (mg) | | Quantity per batch (kg) | |
| Compound I mesylate[1] | | [2]119.500 | | 167.300 | |
| Microcrystalline cellulose[1] | (1.1) | 25.000 | | 35.000 | |
| Hypromellose/ Hydroxypropyl methylcellulose[1] | (1.1) | 2.500 | | 3.500 | |
| Microcrystalline cellulose | [3](1.1) | 9.850 | | 13.790 | |
| Crospovidone | (1.2) | 28.000 | | 39.200 | |
| Silica, colloidal anhydrous/Colloidal silicon dioxide | (1.3) | 1.250 | | 1.750 | |
| Magnesium stearate | (1.4) | 1.400 | | 1.960 | |
| Basic coating premix yellow | (1.5) | 7.125 | 8.550[4] | 9.975 | 14.364[4] |
| Basic coating premix red | (1.5) | 0.375 | 0.450[4] | 0.525 | 0.756[4] |
| Total weight | | 195.000 | 196.500 | 273.000 | ≈275.000 |
| Units/batch | | | | | 1'400'000 |

[1]Components of the granulate,
[2]119.5 mg Compound I mesylate equals 100 mg Compound I free base,
[3]Microcrystalline cellulose is added in the outer phase as a dry binder,
[4]a 20% manufacturing overage of the coating dispersion is included to cover spray losses during the coating process step.

Tablets of 100 mg of Compound I free base according to the invention and of the above tablet were prepared by wet granulation of a mixture of Compound I salt with (1.1), mixing with [3](1.1), (1.2), (1.3) and (1.4), compressing and coating the resultant tablets with an aqueous dispersion of the coating mixture (1.5).

The coating process may be performed at low temperature, e.g. ranging from around 35 to around 38° C. The coating process may be performed with a spray rate preferably in the range of 30 to 105 g of coating dispersion per kg of cores ("core" corresponds to the compressed inner and outer phase) per hour, e.g. 35 to 105 g per kg of cores per h.

Example 2

Tablet Formulation (400 mg Tablet)

Tablets of 400 mg of Compound I according to the invention and of the following tablet were prepared by wet granulation of a mixture of Compound I salt with (1.1), mixing with [3](1.1), (1.2), (1,3) and (1.4), compressing and coating the resultant tablets with as aqueous dispersion of the coating mixture (1.5).

| Composition per dosage form unit and quantity per batch | | | | | |
|---|---|---|---|---|---|
| Component | | Composition per unit (mg) | | Quantity per batch (kg) | |
| Compound I mesylate[1] | | [2]478.000 | | 167.300 | |
| Microcrystalline cellulose[1] | (1.1) | 100.000 | | 35.000 | |
| Hypromellose/ Hydroxypropyl methylcellulose[1] | (1.1) | 10.000 | | 3.500 | |
| Microcrystalline cellulose[3] | (1.1) | 39.400 | | 13.790 | |
| Crospovidone | (1.2) | 112.000 | | 39.200 | |
| Silica, colloidal anhydrous/Colloidal silicon dioxide | (1.3) | 5.000 | | 1.750 | |
| Magnesium stearate | (1.4) | 5.600 | | 1.960 | |
| Basic coating premix yellow | (1.5) | 17.100 | 20.425[4] | 5.985 | 8.588[4] |
| Basic coating premix red | (1.5) | 0.900 | 1.075[4] | 0.315 | 0.452[4] |
| Total weight | | 768.000 | 771.500 | 268.800 | ≈270.000 |
| Units/batch | | | | | 350'000 |

[1]Components of the granulate,
[2]478 mg Compound I mesylate equals 400 mg Compound I free base,
[3]Microcrystalline cellulose is added in the outer phase as a dry binder,
[4]a 20% manufacturing overage of the coating dispersion is included to cover spray losses during the coating process step.

The coating process may be performed at low temperature, e.g. ranging from around 35 to around 38° C. The coating process may be performed with a spray rate preferably in the range of 30 to 105 g of coating dispersion per kg of cores ("core" corresponds to the compressed inner and outer phase) per hour, e.g. 35 to 105 g per kg of cores per h.

Example 3

Dimensions of the Tablets

| Compound I free base/tablet | Shape and Dimensions |
|---|---|
| 100 mg | Round, 9.1-9.3 mm diameter, curved, bevelled edges, thickness: 2.8-3.4 mm break score on one side |
| 400 mg | Ovaloid, 18.1-18.3 × 7.2-7.4 mm, curved, bevelled edges, thickness: 6.6-7.2 mm |

| Compound I free base/tablet | Shape and Dimensions |
|---|---|
| 100 mg | Round, 9.1-9.4 mm diameter, curved, bevelled edges, thickness: 2.8-3.4 mm break score on one side |
| 400 mg | Ovaloid, 18.1-18.4 × 7.2-7.5 mm, curved, bevelled edges, thickness: 6.6-7.2 mm |

The invention claimed is:

1. A small tablet comprising a pharmacologically effective amount of 4-(4-methylpiperazin-1-ylmethyl)-N-[4-methyl-3-(4-pyridin-3-yl)pyrimidin-2-ylamino)phenyl]-benzamide of formula (1) in the form of a monomesylate salt as the sole active drug:

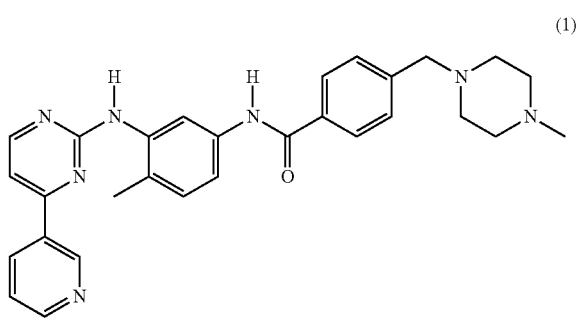 [SMILES: Cc1ccc(NC(=O)c2ccc(CN3CCN(C)CC3)cc2)cc1Nc1nccc(-c2cccnc2)n1]

in an amount from 30% to 80% by weight of the active moiety based on the total weight of the small tablet; and 10 to 35% by weight of at least one disintegrant based on the weight of the small tablet, wherein the at least one disintegrant is cross-linked polyvinlypyrrolidinone, wherein the small tablet is either a small ovaloid tablet that is 10 to 20 mm in length, 5 to 10 mm in width and 4 to 8 mm in thickness or a small round tablet that is 5 to 15 mm in diameter and 2 to 5 mm in thickness and wherein the pharmacologically effective amount of the sole active moiety 4-(4-methylpiperazin-1-ylmethyl)-N-[4-methyl-3-(4-pyridin-3-yl)pyrimidin-2-ylamino)phenyl]-benzamide is from 50 mg to 600 mg.

2. A small tablet according to claim 1, wherein the sole active moiety is present in an amount from 50% to 80% of the active moiety by weight based on the total weight of the small tablet.

3. A small tablet according to claim 1 wherein the 4-(4-methylpiperazin-1-ylmethyl)-N-[4-methyl-3-(4-pyridin-3-yl)pyrimidin-2-ylamino)phenyl]-benzamide monomesylate salt is in the alpha crystalline form thereof.

4. A small tablet according to claim 1 wherein 4-(4-methylpiperazin-1-ylmethyl)-N-[4-methyl-3-(4-pyridin-3-yl)pyrimidin-2-ylamino)phenyl]benzamide monomesylate is in the beta crystalline form thereof.

5. A small tablet according to claim 1 further comprising at least one binder.

6. The small tablet according to claim 1 further comprising:
at least one binder in an amount of 1% to 25% in weight based on the total weight of the small tablet;
at least one glidant in an amount of 0.5% to 3% in weight based on the total weight of the small tablet; and/or
at least one lubricant in an amount of 0.5% to 2% in weight based on the total weight of the small tablet and wherein the small ovaloid tablet comprises 400 mg of 4-(4-methylpiperazin-1-ylmethyl)-N-[4-methyl-3-(4-pyridin-3-pyrimidin-2-ylamino)phenyl]-benzamide and the small round tablet comprises 100 mg of 4-(4-methylpiperazin-1-ylmethyl)-N-[4-methyl-3-(4-pyridin-3yl)pyrimidin-2-ylamino)phenyl]-benzamide.

7. A small tablet according to claim 6 wherein the binder is selected from: microcrystalline cellulose, hydroxypropylcellulose and mixtures thereof.

8. A small tablet according to claim 6 wherein the glidant is selected from: colloidal silicon dioxide, colloidal anhydrous silica and mixtures thereof.

9. A small tablet according to claim 6 wherein the lubricant is magnesium stearate.

10. A process for the preparation of a small tablet according to claim 5, which process comprises
(a) forming an inner phase comprising
(i) mixing the sole active drug 4-(4-methylpiperazin-1-ylmethyl)-N-[4-methyl-3-(4-pyridin-3-yl)pyrimidin-2-ylamino)phenyl]-benzamide of formula (1)) in the form of monomesylate salt and at least one binder, wherein the active moiety of 4-(4-methylpiperazin-1-ylmethyl)-N-[4-methyl-3-(4-pyridin-3-yl)pyrimidin-2-ylamino)phenyl]-benzamide is 30 to 80% based on the total weight of the small tablet;
(ii) wet-granulating;
(b) forming an outer phase comprising
(iii) mixing with 10 to 35% by weight of at least one disintegrant based on the total weight of the small tablet, wherein one disintegrant is cross-linked polyvinylpyrrolidone; to form a mixture; and
(c) forming a tablet by
(iv) compressing the mixture obtained in step (iii).

11. The process of claim 10 further comprising coating the tablet formed in (iv) at a low temperature of between 30 and 40 degrees C.

* * * * *